United States Patent
Collins

(10) Patent No.: US 10,125,163 B2
(45) Date of Patent: *Nov. 13, 2018

(54) SOLID PHASE PEPTIDE SYNTHESIS

(71) Applicant: CEM Corporation, Matthews, NC (US)

(72) Inventor: Jonathan M. Collins, Charlotte, NC (US)

(73) Assignee: CEM Corporation, Matthews, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/299,931

(22) Filed: Oct. 21, 2016

(65) Prior Publication Data

US 2017/0226152 A1    Aug. 10, 2017

Related U.S. Application Data

(60) Provisional application No. 62/245,484, filed on Oct. 23, 2015.

(51) Int. Cl.
*B01J 19/12* (2006.01)
*C07K 1/04* (2006.01)
(Continued)

(52) U.S. Cl.
CPC ............ *C07K 1/045* (2013.01); *B01J 19/126* (2013.01); *C07K 1/063* (2013.01); *C07K 1/1075* (2013.01);
(Continued)

(58) Field of Classification Search
CPC ...... B01J 4/00; B01J 19/126; B01J 2204/005; B01J 2208/00; C07K 1/04; C07K 1/045
See application file for complete search history.

(56) References Cited

U.S. PATENT DOCUMENTS

| 6,288,379 B1 | 9/2001 | Greene et al. |
| 7,393,920 B2 | 7/2008 | Collins |
| (Continued) | | |

FOREIGN PATENT DOCUMENTS

| WO | WO-2014033297 A1 * | 3/2014 | .......... B01F 11/0002 |
| WO | 2015028599 | 3/2015 | |
| WO | 2017070512 | 4/2017 | |

OTHER PUBLICATIONS

Sampson, JH et al. An epidermal growth factor receptor variant III—targeted vaccine is safe and immunogenic in patients with glioblastoma multiforme. Mol. Cancer Ther. 2009; 8: 2773-2779.

(Continued)

*Primary Examiner* — Jeffrey E. Russel
(74) *Attorney, Agent, or Firm* — Parsons Summa

(57) ABSTRACT

An improved method of deprotection in solid phase peptide synthesis is disclosed. In particular the deprotecting composition is added in high concentration and small volume to the mixture of the coupling solution, the growing peptide chain, and any excess activated acid from the preceding coupling cycle, and without any draining step between the coupling step of the previous cycle and the addition of the deprotection composition for the successive cycle. Thereafter, the ambient pressure in the vessel is reduced with a vacuum pull to remove the deprotecting composition without any draining step and without otherwise adversely affecting the remaining materials in the vessel or causing problems in subsequent steps in the SPPS cycle.

14 Claims, 5 Drawing Sheets

Specification includes a Sequence Listing.

(51) Int. Cl.
C07K 1/107 (2006.01)
C07K 1/14 (2006.01)
C07K 1/06 (2006.01)
C07K 14/575 (2006.01)
C07K 14/605 (2006.01)
C07K 14/815 (2006.01)
C07K 14/635 (2006.01)
C07K 14/59 (2006.01)
C07K 14/705 (2006.01)
C07K 14/645 (2006.01)
C07K 14/005 (2006.01)
C12N 7/00 (2006.01)
C07K 14/47 (2006.01)
C07K 7/08 (2006.01)
C07K 7/16 (2006.01)
C07K 14/46 (2006.01)

(52) U.S. Cl.
CPC ............... C07K 1/14 (2013.01); C07K 7/08 (2013.01); C07K 7/16 (2013.01); C07K 14/005 (2013.01); C07K 14/463 (2013.01); C07K 14/4701 (2013.01); C07K 14/4723 (2013.01); C07K 14/575 (2013.01); C07K 14/57572 (2013.01); C07K 14/59 (2013.01); C07K 14/605 (2013.01); C07K 14/635 (2013.01); C07K 14/645 (2013.01); C07K 14/705 (2013.01); C07K 14/815 (2013.01); C12N 7/00 (2013.01); B01J 2204/005 (2013.01); B01J 2219/00058 (2013.01); B01J 2219/0879 (2013.01); B01J 2219/1248 (2013.01); C12N 2740/16322 (2013.01)

(56) References Cited

U.S. PATENT DOCUMENTS

| 7,803,351 B2* | 9/2010 | Sharma | A61K 49/0002 424/1.11 |
|---|---|---|---|
| 2004/0238794 A1* | 12/2004 | Karandikar | B01J 19/126 252/500 |
| 2007/0270573 A1 | 11/2007 | Collins | |
| 2012/0041173 A1 | 2/2012 | Collins | |
| 2013/0034547 A1* | 2/2013 | Kelly | C07K 1/1077 424/133.1 |
| 2014/0275481 A1 | 9/2014 | Simon | |

OTHER PUBLICATIONS

Li G, Siddhartha M, Wong AJ. The epidermal growth factor variant III peptide vaccine for treatment of malignant gliomas. Neurosurg. Clin. N. Am. 2010; 21: 87-93.
Li G, Wong AJ. EGF receptor variant III as a target antigen for tumor immunotherapy. Expert Rev. Vaccines 2008; 7: 977-985.
R. B. Merrifield; Solid Phase Peptide Synthesis. I. The Synthesis of a Tetrapeptide; J. Am. Chem. Soc., 1963, 85(14), pp. 2149-2154.
Chan and White, Fmoc Solid Phase Peptide Synthesis, Oxford University Press 2000, p. 1.
Collins, Microwave-enhanced solid-phase peptide synthesis. ChemInform, 39(46) i. 2008.
Bacsa et al., Rapid solid-phase peptide synthesis using thermal and controleld microwave irradiation; Journal Peptide Science, 2006, 12(10), 633-638.
Amblard et al., Methods and protocols of modern solid phase peptide synthesis, Molecular Biotechnology, 2006, 239-254.
Coin et al., Solid-phase peptide synthesis: from standard procedures to the synthesis of difficult sequences; Nature Protocols, 2007, 2(12), 3247-3256.
J. Collins, K. Porter, S. Singh and G. Vanier, "High-Efficiency Solid Phase Peptide Synthesis (HE-SPPS)," Org. Lett., vol. 16, pp. 940-943, 2014.
M. Beyermann, P. Henklein, A. Klose, R. Sohr and M. Bienert, "Effect of tertiary amine on the carbodiimide-mediated peptide synthesis," Int. J. Peptide Protein Res., vol. 37, pp. 252-256, 1991.
L. Carpino, El-Faham and A., "The Diisopropylcarbodiimide/1-Hydroxy-7-azabenzotriazole System: Segment Coupling and Step-wise Peptide Assembly," Tetrahedron, vol. 55, pp. 6813-6830, 1999.
E. Atherton, N. L. Benoiton, E. Brown, R. Sheppard and B. J. Williams, "Racemization of Activaterd, Urethane-protected Amino-acids by p-Dimethylaminopyridine. Significance in Solid-phase Peptide Synthesis," J.C.S. Chem. Comm., pp. 336-337, 1981.
S. Wang, J. Tam, B. Wang and R. Merrifield, "Enhancement of peptide coupling reactions by 4-dimethylaminopyridine," Int. J. Peptide Protein Res., vol. 18, pp. 459-467, 1981.
M. Pennington, "Procedures to Improve Difficult Couplings," in Peptide Synthesis Protocols, Vols. Methods in Molecular Biology—vol. 35, Totowa, NJ, Humana Press, 1995, p. 10.
X. Shangjie, I. Held, B. Kempf, H. Mayr, W. Steglich and H. Zipse, "The DMAP-Catalyzed Acetylation of Alcohols—A Mechanistic Study," Chemistry, vol. 11, pp. 4751-4757, 2005.
P. White, J. Collins and Z. Cox, "Comparative study of conventional and microwave assisted synthesis," in 19th American Peptide Symposium, San Diego, CA, 2005.
A. Tofteng, S. Pedersen, D. Staerk and K. Jensen, "Effect of Residual Water and Microwave Heating on the Half-Life of the Reagents and Reactive Intermediates in Peptide Synthesis," Chemistry, vol. 18, pp. 9024-9031, 2012.
K. Wehrstedt, P. Wandrey and D. Heitkamp, "Explosive properties of 1-hydroxybenzotriazoles," J. Hazard Mater, vol. 126, pp. 1-7, 2005.
M. Itoh, "Peptides. IV. Racemization Suppression by the Use of Ethyl-2-Hydroximino-2-cyanoacetate and Its Amide," Bull. Chem. Soc. Jpn., vol. 46, pp. 2219-2221, 1973.
J. Perich, N. Ede, S. Eagle and A. Bray, "Synthesis of phosphopeptides by the Multipin method: Evaluation of coupling methods for the incorporation of Fmoc-Tyr(PO3BzI,H)-OH, Fmoc-Ser(PO3BzI,H)-OH and Fmoc-Thr(PO3BzI,H)-OH," Lett. Pept. Sci., vol. 6, pp. 91-97, 1999.
L. Carpino and A. El-Faham, "Effect of Teriary Bases on O-Benzotriazolyuronium Salt-Induced Peptide Segment Coupling," J. Org. Chem., vol. 59, pp. 695-698, 1994.
T. Lescrinier, R. Busson, H. Winter, C. Hendrix, G. Janssen, C. Pannecouque, J. Rozenski, A. Aerschot and P. Herdewijn, "a-Amino acids derived from omithine as building blocks for peptide synthesis," J. Pept. Res., vol. 49, pp. 183-189, 1997.
S. Nozaki, "Delay of coupling caused by excess additives," J. Pept. Sci., vol. 12, pp. 147-153, 2006.
R. Subirós-Funosas, R. Prohens, R. Barbas, A. El-Faham and F. Albericio, "Oxyma: An Efficient Additive for Peptide Synthesis to Replace the Benzotriazole-Based HOBt and HOAt with a Lower Risk of Explosion," Chemistry, vol. 15, pp. 9394-9403, 2009.
M. Cezari and L. Juliano, "Studies on lactam formation during coupling procedures of N alpha-N omega-protected arginine derivatives," J. Pept. Res., vol. 9, pp. 88-91, 1996.
I. Friligou, E. Papadimitriou, D. Gatos, J. Matsoukas and T. Tselios, "Microwave-assisted solid-phase peptide synthesis of the 60-110 domain of human pleiotrophin on 2-chlorotrityl resin," Amino Acids, vol. 40, pp. 1431-1440, 2011.
R Subirós-Funosas, "Use of Oxyma as pH modulatory agent to be used in the prevention of base-driven side reactions and its effect on 2-chlorotrityl chloride resin," Pept. Sci., vol. 98, pp. 89-97, 2012.
International Search Report of counterpart Application No. PCT/US2016/058181 dated Jan. 31, 2017.
Finneman et al., "Novel approach for optimization of a 'difficult' peptide synthesis by utilizing quantitative reaction monitoring assays," J. Pept. Sci., 2012; 18: 511-518.
CEM Corporation, Microwave Synthesis of 'difficult' peptide EGFRvIII; 2013; 3 pages.
Counterpart U.S. Appl. No. 15/490,090, filed Apr. 18, 2017 entitled "In-Situ Solvent Recycling Process for Solid Phase Peptide Synthesis at Elevated Temperatures".

(56) References Cited

OTHER PUBLICATIONS

Counterpart International Patent Application No. PCTUS2017028254 filed Apr. 19, 2017 entitled "In-Situ Solvent Recycling Process for Solid Phase Peptide Synthesis at Elevated Temperatures".

International Search Report of counterpart Application No. PCT/US2017/028254 dated Aug. 1, 2017.

Palasek, et al., Limiting racemization and aspartimide formation on microwave-enhanced Fmoc solid phase peptide synthesis; J. Pept. Sci., 2006; 13: 143-148.

J. Collins, "Microwave-Enhanced Synthesis of Peptides, Proteins, and Peptidomimetics," in Microwaves in Organic Synthesis' 3rd Ed., Weinheim, Germany, Wiley-VCH Verlag & Co KGaA, 2013, pp. 897-960.

Methods for determining enantiomeric purity of amino acids; accessed Oct. 4, 2017 at http://cat-online.com/enantiomeric%20purity.html.

\* cited by examiner

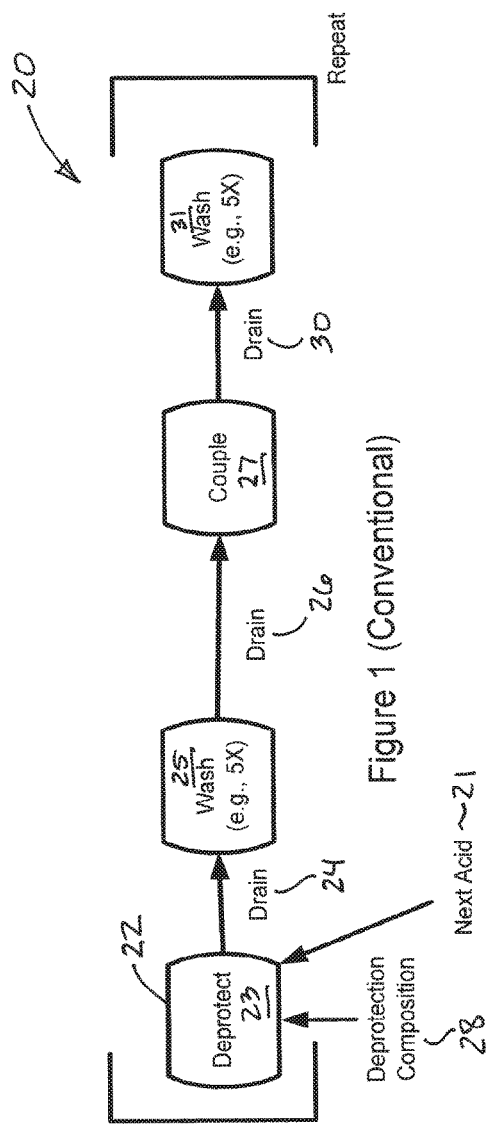
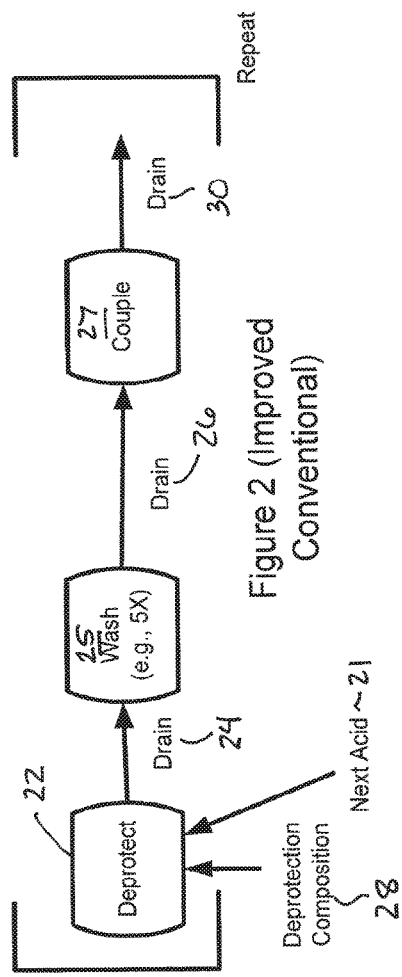
Figure 1 (Conventional)
Figure 2 (Improved Conventional)

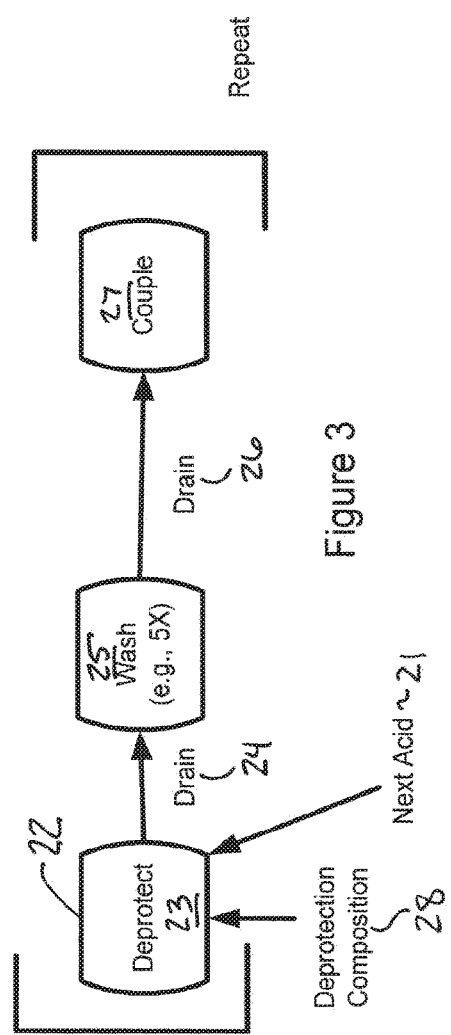
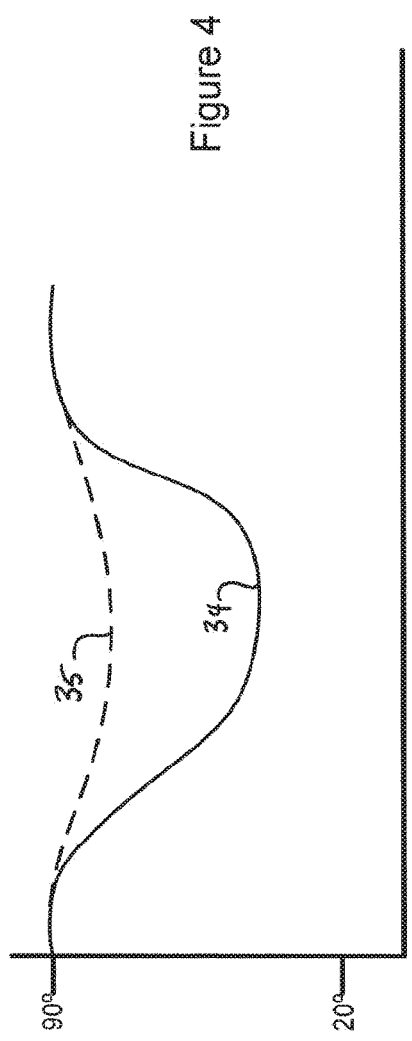

SOLID PHASE PEPTIDE SYNTHESIS

REFERENCE TO SEQUENCE LISTING

This application incorporates by reference the sequence listing submitted on Jul. 10, 2018 in ASCII text file format in accordance with 37 CFR 1.824(a) titled "20180625_amended_sequence_listing" created on Jun. 25, 2018 with a file size of 8 KB. The sequence listing is part of the specification and is herein incorporated by reference in its entirely. In accordance with 37 CFR 1.825(a), the sequence listing contains no new matter.

The present invention relates to improvements in the solid phase synthesis of peptides ("SPPS").

Peptides are linked chains of amino acids which in turn are the basic building blocks for most living organisms. Peptides are also the precursors of proteins; i.e., long complex chains of amino acids. Peptides and proteins are fundamental to human and animal life, and they drive, affect, or control a wide variety of natural processes.

As just one example, peptides have been recently identified that can "keyhole" tumor specific mutations in certain cancers and thus act as tumor specific vaccines (e.g., SAMPSON, J H ET AL. *An epidermal growth factor receptor variant III-targeted vaccine is safe and immunogenic in patients with glioblastoma multiforme*. Mol. Cancer Ther. 2009; 8: 2773-2779; Li G, SIDDHARTHA M, WONG A J. *The epidermal growth factor variant III peptide vaccine for treatment of malignant gliomas*. Neurosurg. Clin. N. Am. 2010; 21: 87-93; LI G, WONG A J. *EGF receptor variant III as a target antigen for tumor immunotherapy*. Expert Rev. Vaccines 2008; 7: 977-985).

As a result, the study of peptides and proteins and the capability to synthesize peptides and proteins are of significant interest in the biological sciences and medicine.

In concept, solid phase synthesis is relatively simple and straightforward. An amino acid is attached to a solid phase particle by a linking group on the acid side, and to a protecting group on the amine side. The protecting group is removed so that the second acid (and in particular its acid group) can be coupled to the amine group on the original acid. The second (and succeeding) acids are also initially protected, and thus the general sequence is to deprotect, couple, and repeat until the desired peptide is completed, following which the completed peptide is cleaved from the solid phase resin.

Solid phase peptide synthesis had its genesis in 1963 when R. B. Merrifield published the synthesis of a four-acid chain using a solid phase method (R. B. MERRIFIELD; *Solid Phase Peptide Synthesis. I. The Synthesis of a Tetrapeptide*; J. Am. Chem. Soc., 1963, 85 (14), pp 2149-2154).

At the time, it was generally recognized that organic reactions could be carried out in this manner, but it was assumed that the Merrifield method would be difficult to adapt to longer peptide sequences in any realistic purity. Specifically, Merrifield's suggestion that the isolation steps between and among coupling and deprotection steps could be carried out merely by washing and without identification of intermediates, was considered unlikely to offer long-term success. In peptide synthesis, two problems are characteristic: (1) the synthesis of unwanted byproducts; and (2) the synthesis of some fraction of an undesired sequence based on the presence of unremoved acid from a previous step or cycle. In particular, a residue of the recently added ("activated") acid tends to remain after the coupling step and must accordingly be removed in some fashion.

Nevertheless, as summarized by CHAN AND WHITE, *Fmoc Solid Phase Peptide Synthesis* (Oxford University Press 2000), the washing steps provide acceptable purity and the general simplicity of those washing steps and of avoiding detailed characterization of intermediates gives the SPPS method its speed and efficiency advantages (e.g., page 1).

Accordingly, as generally well understood in the art, the SPPS deprotection step is typically carried out by adding an organic base to the protected acid, then draining the reaction vessel—one of the advantages of SPPS is that the organic compounds can be handled as if they were solids—then washing the deprotected chain. In most circumstances, a wash repeated five times is both typical and satisfactory to remove anything that might create different sequences or undesired byproducts. The coupling step is then carried out followed by another draining step, and another repetitive wash, with five washes again being typical.

More recently (e.g., U.S. 20120041173; the contents of which are incorporated entirely herein by reference), it has become recognized that adding the deprotecting base for the next cycle will scavenge the activated acid remaining from the previous cycle, thus reducing or eliminating the number of washing cycles necessary to ensure purity and avoid unwanted sequences.

To interject with a point well understood in this art, improving, accelerating or eliminating any of the SPPS steps becomes geometrically advantageous as longer peptide sequences are synthesized. In this regard, microwave assisted techniques have become widely accepted in the art, following their introduction about a decade ago (e.g., commonly assigned U.S. Pat. No. 7,393,920, the contents of which are likewise incorporated entirely herein by reference). Microwave techniques have reduced cycle times from hours to minutes, thus providing multiple advantages in SPPS and in research or commerce that depends upon SPPS.

To the extent that a newer technique such as microwave assisted solid phase peptide synthesis can be called typical or conventional, the step of adding the deprotecting base is usually carried out by adding a sufficient volume of relatively low concentration that will cover the drained resin in the reaction vessel and the attached peptide after the coupling step to ensure that both the scavenging and deprotection reactions take place.

Doing so, however, creates a thermal slow down (so to speak) in that the volume of dilute organic base solution is added at room temperature (e.g.,) 25° while the coupling step has just been carried out at an elevated temperature, of which temperatures of about 90° C. are exemplary (although not limiting). As expected in a normal heat transfer situation, this reduces the overall temperature of the components in the vessel, which then must be reheated to reach the reaction temperature required for the next deprotection and coupling cycle.

Although these characteristics are disadvantageous only in the strictest sense, an overall advantage always exists when steps in the SPPS cycle are enhanced, accelerated, or simply rendered unnecessary. Such improvements become more and more advantageous (and conventional methods become more disadvantageous) as the peptide chain length increases. Thus, speed advantages that might remain proportionally meaningless in conventional organic solid phase reactions (i.e., those that require only a few, and perhaps only a single solid phase step) become increasingly important when peptides containing 10, 20, or more acids are synthesized using SPPS.

SUMMARY

In one aspect the invention is a method of deprotection in solid phase peptide synthesis in which the improvement comprises adding the deprotecting composition in high concentration and small volume to the mixture of the coupling solution, the growing peptide chain, and any excess activated acid from the preceding coupling cycle, and without any draining step between the coupling step of the previous cycle and the addition of the deprotection composition for the successive cycle.

In another aspect the invention is a method of deprotection in solid phase peptide synthesis in which the improvement comprises deprotecting a protected amino acid by combining the protected amino acid and a liquid organic base in a reaction vessel and during or after the deprotection step reducing the ambient pressure in the vessel with a vacuum pull to remove the liquid organic base without any intermediate draining step.

In another aspect the invention is a method of deprotection in solid phase peptide synthesis (SPPS) in which the improvement comprises deprotecting a protected amino acid at a temperature of at least about 60° C. while providing a path for evaporating base to leave the reaction vessel In another aspect the invention is a system for microwave assisted solid phase peptide synthesis. In this aspect, the system includes a microwave source positioned to direct microwave radiation into a microwave cavity, a microwave transparent reaction vessel in the cavity, and a vacuum source connected to the reaction vessel.

In another aspect the invention is a method of deprotection in solid phase peptide synthesis in which the improvement comprises adding the deprotecting composition in high concentration and small volume to the mixture of the coupling solution, the growing peptide chain, and any excess activated acid from the preceding coupling cycle, and without any draining step between the coupling step of the previous cycle and the addition of the deprotection composition for the successive cycle, and thereafter reducing the ambient pressure in the vessel with a vacuum pull to remove the deprotecting composition without any draining step.

In another aspect the invention is a method of deprotection in solid phase peptide synthesis which includes the steps of adding the deprotection composition in high concentration and small volume to the mixture of the coupling solution, the growing peptide chain, and any excess activated amino acid from the preceding coupling cycle; and without any draining step between the coupling step of the previous cycle and the addition of the deprotection composition for the successive cycle which removes at least 50% of the volume of the previous cycle coupling solution; and with the coupling solution at least 30° C.

The foregoing and other objects and advantages of the invention and the manner in which the same are accomplished will become clearer based on the followed detailed description taken in conjunction with the accompanying drawings.

BRIEF DESCRIPTION OF THE DRAWINGS

FIG. 1 is a schematic diagram of the conventional steps of SPPS synthesis.

FIG. 2 is a schematic diagram of an improved version of conventional SPPS peptide synthesis.

FIG. 3 is a schematic diagram of a first embodiment of the present invention.

FIG. 4 is a diagram illustrating the thermal advantages of the current invention.

DETAILED DESCRIPTION

Figure 5:
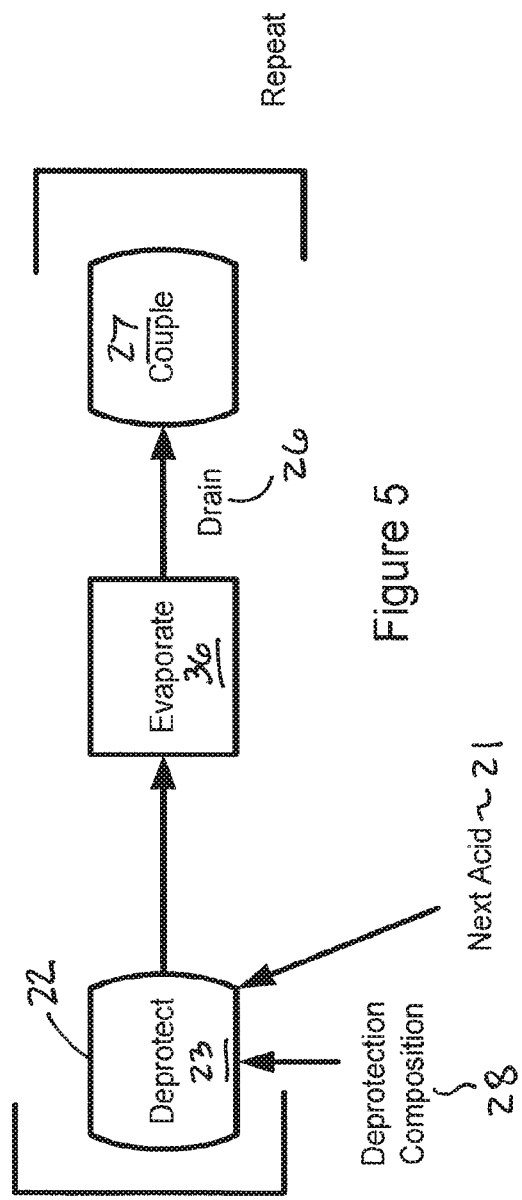
FIG. 5 is a schematic diagram of a second embodiment of the invention.

FIG. 1 is a schematic diagram of a conventional cycle repeated during solid phase peptide synthesis and broadly designated at 20. As set forth therein, the next acid to be added 21 is added in protected fashion to a reaction vessel schematically diagramed at 22. The deprotection step 23 is carried out in the vessel 22 by adding an organic base in a concentration of about 20% by volume in dimethyl formamide (DMF). Useful organic bases include, but are not limited to piperidine ($C_5H_{11}N$; CAS No 110-89-4), pyrrolidine ($C_4H_9N$; CAS No 123-75-1), and 4-methyl piperidine ($C_6H_{13}N$; CAS No. 626-58-4). As indicated by the position of the relative arrows, the deprotection solution 28 is added in advance of the next acid.

The deprotection solution is then drained (step 24) following which a washing liquid (e.g., methanol or isopropanol) is added to the vessel for a washing step 25 carried out repetitively with five repetitions being typical. The washing solution is then removed in a second draining step 26 which allows the coupling step 27 to take place. The coupling composition is then removed in a third draining step 30 followed by a second washing step 31, again repeated five times.

It will be understood that FIG. 1 is schematic, and that there are many details about one SPPS cycle that could be added, but that FIG. 1 illustrates the concept sufficiently for the skilled person to understand both it and the present invention. In particular, the skilled person already recognizes that FIG. 1 represents a cycle that is neither the step of linking the resin to the first acid, nor does it illustrate cleaving a finished peptide from the resin.

FIG. 2 illustrates the improved conventional method referred to in the Background. In particular, the last washing step 31 of FIG. 1 can be omitted because any excess acid left after the coupling step 27 will be quenched by the deprotection solution (base) added at the start of the next cycle. Obviously, this requires that deprotection solution be added before the next acid 21 is added to the vessel 22.

FIG. 3 illustrates a first embodiment of the invention in which the improvement comprises adding the deprotection composition in a high concentration and small volume to the mixture of the coupling solution, the growing peptide chain, and any excess activated acid from the preceding coupling cycle, and doing so without any draining step between the coupling step of the previous cycle and the addition of the deprotection composition for the successive cycle.

The use of a small volume in high concentration saves physical space (only a small bottle is needed), avoids the need to prepare a solution, and saves solvent. The method additionally offers a thermal advantage (FIG. 3).

In exemplary versions of the claimed invention, an organic base is used as the deprotecting composition with piperidine or pyrrolidine or 4-methylpiperidine being typical (although not necessarily exclusive) for this purpose. It will be understood, of course, that additional organic bases that provide the deprotection function without otherwise interfering with the other steps in the method, the growing peptide chain, or the instrument, will be appropriate as well.

In the most exemplary embodiment, the piperidine or pyrrolidine or 4-methylpiperidine can be added neat; i.e. as an organic liquid and not in solution. In other circumstances, the piperidine or pyrrolidine or 4-methylpiperidine can be added as a highly concentrated solution of at least about 50% organic base by volume, typically in DMF.

As a further advantage, the high concentration allows the organic base to be added in a proportionally small volume with a ratio of between about 1:20 and 1:3 being appropriate based upon the volume of the coupling solution. Piperidine or pyrrolidine or 4-methylpiperidine can be added in the volume ratio of about 1:5 based upon the volume of the coupling solution when added neat. In such circumstances, the small volume of the deprotecting solution is typically less than 2 ml, and often less than one milliliter. In exemplary circumstances, between about 0.4 and 1.0 ml of piperidine are added to between about 3.8 and 4.2 ml of the mixture of the coupling solution, the growing peptide chain and any excess activated acid.

Expressing the proportion as a percentage, the small volume of the deprotecting solution is 20% or less of the volume of the mixture of the coupling solution, the growing peptide chain, and any excess activated acid.

FIG. 4 illustrates the thermal advantage offered by the invention which provides an additional time advantage in each SPPS cycle. As FIG. 4 demonstrates, if the coupling step is carried out at temperatures of about 90° C., the conventional use of a room temperature (e.g. 25° C.) wash will have the expected thermal effect of lowering the temperature of peptide and the resin in the vessel in accordance with well understood and relatively simple relationships (e.g., the drop in temperature will be directly proportional to the mass of the added cooler liquid). Thus, when a washing or draining step is carried out after coupling, there will be some time interval required to bring the reacting compositions back up to the 90° coupling temperature.

In the invention, however, the addition of a small volume (mass) of concentrated base will greatly moderate the degree to which the temperature drops, thus making it easier and faster to return the compositions to the required coupling temperatures. In FIG. 4, the conventional thermal profile is indicated by the solid line 34 and the thermal profile provided by the invention is indicated by the dotted line 35. It will be understood, of course, that FIG. 4 is schematic, not drawn to scale, and illustrative rather than a precise track of any particular mixture.

FIG. 5 illustrates another aspect of the invention in which the improvement comprises deprotecting a protected amino acid by combining the protected amino acid and liquid organic base in a reaction vessel, and then during or after the deprotection step reducing the ambient pressure in the vessel to below atmospheric pressure with a vacuum pull to remove the liquid organic base without any intervening draining step.

In general, and as can be confirmed by appropriate resources, the boiling point of piperidine is approximately 106° C. and that of DMF is about 153° C. As a result the vapor pressure of piperidine will be higher than the vapor pressure of DMF at any given temperature. Accordingly it has now been discovered that pulling a moderate vacuum from the vessel can selectively remove the piperidine and completely avoid the draining step. FIG. 5 illustrates this schematically by showing the deprotection step 23 followed by an evaporation step 36 followed by the draining step (of liquids other than the organic base) and then the coupling step 27. The boiling point of 4-methylpiperidine is 123° C., offering similar advantages.

Expressed alternatively, piperidine's vapor pressure is about 4 mm Hg at 25° C., about 39 mm Hg at 50° C., and about 55 mm Hg at 60° C. For pyrrolidine, the vapor pressure is about 8.4 mm Hg at 25° C. and about 102 mm Hg at 60° C. Thus, raising the temperature to 60° C. greatly encourages the desired evaporation.

Consistent with well understood principles of liquid and vapor pressure, the method can further comprise accelerating the deprotection step by heating the combined protected amino acid and the liquid organic base in the vessel 22, and then accelerating the removal step further by pulling the vacuum 36 while heating the vessel contents. When using a microwave assisted process as described herein (and elsewhere), the microwave radiation can be used to both accelerate the deprotection step and to accelerate the vacuum removal step.

In exemplary methods, the pressure can be reduced to below atmospheric pressure, or, expressed in terms of temperatures, the deprotection step can be carried out by heating the compositions to at least about 60° C., and in some cases to between about 81° C. and 99° C., after which the vessel contents can be heated to between about 90° and 110° to accelerate the vacuum removal step. Functionally, the vacuum and the applied microwave power should provide the intended enhanced evaporation without otherwise adversely affecting the remaining materials in the vessel or causing problems in subsequent steps in the SPPS cycle.

These two improvements in overall SPPS cycles can, be combined, so that in another aspect, the improvement includes the steps of adding the deprotecting composition in high concentration and small volume to the mixture of the coupling solution, the growing peptide chain, and any excess activated acid from the preceding coupling step, and doing so without any intervening draining step between the coupling step of the previous cycle and the addition of deprotection composition for the successive cycle. Thereafter, the ambient pressure in the vessel is reduced with a vacuum pull to remove the deprotecting composition without any draining step.

Combining both improvements in this manner is illustrated by the differences between FIG. 1 and FIG. 5 and can allow the cycle to avoid both the washing steps and two of the draining steps. As set forth in the Background, any such advantage in an individual cycle will be geometrically multiplied as a longer peptide chain is synthesized.

Figure 6:
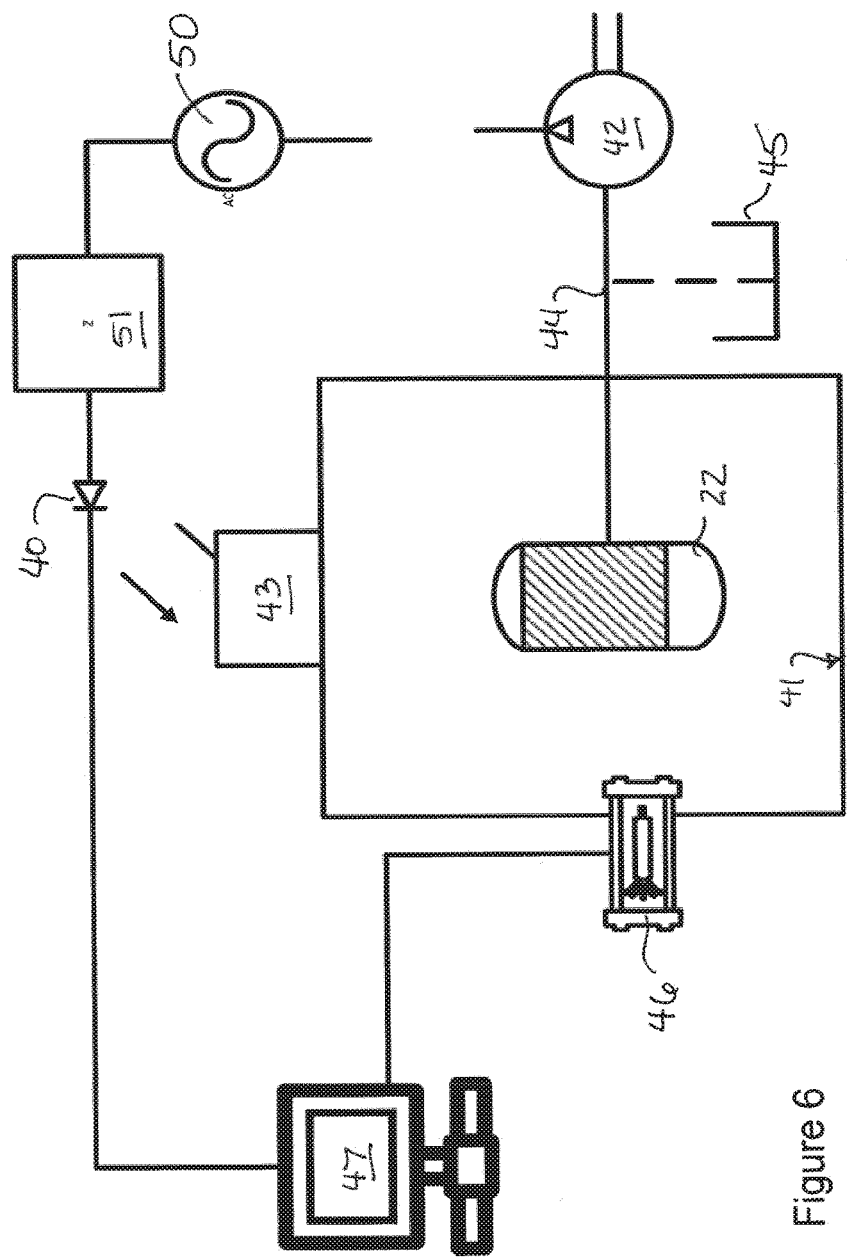
FIG. 6 is a schematic diagram of an instrument used to carry out the method of the present invention.
Figure 7:
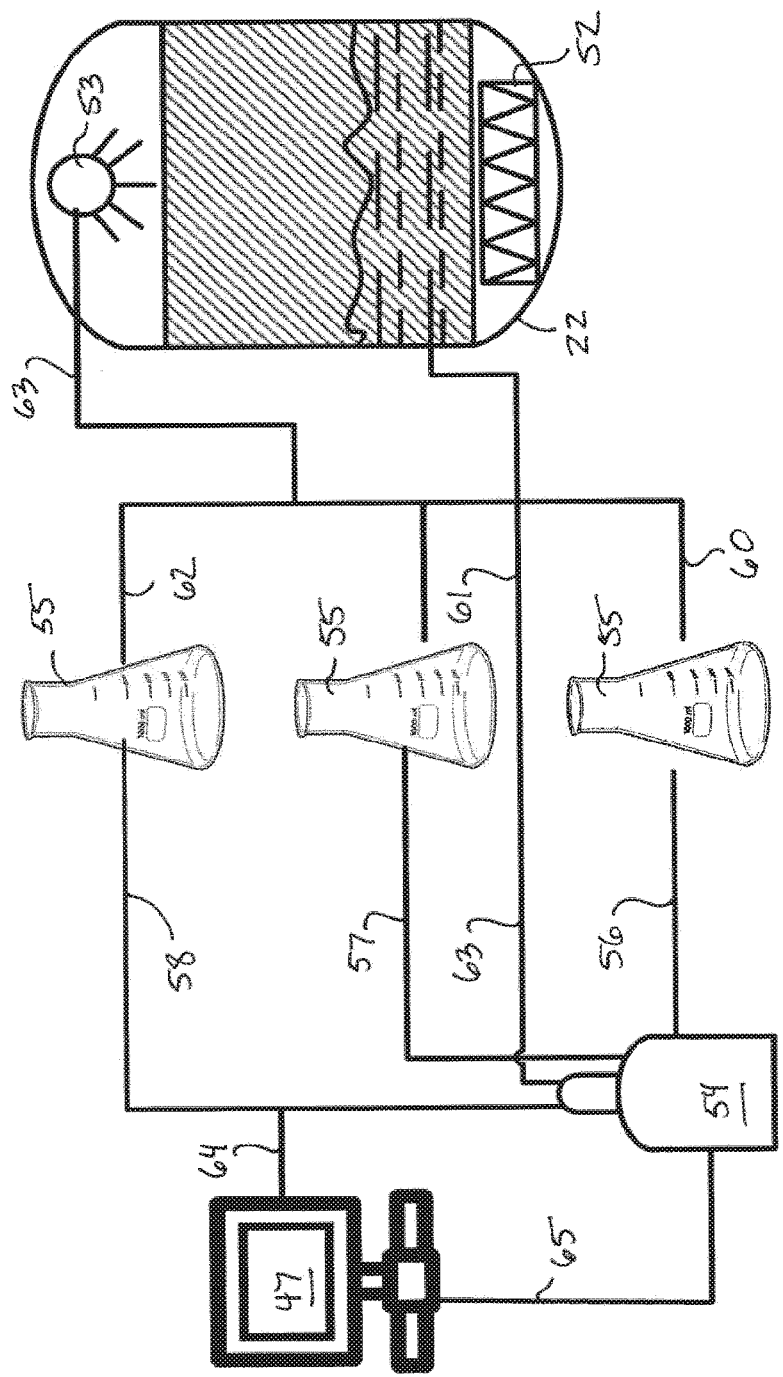
FIG. 7 is a second schematic diagram of portions of the instrument used to carry out the present invention.

FIGS. 6 and 7 are schematic illustrations of selected portions of a system for carrying out the improvements described herein. Most basically, the system includes a microwave source illustrated as the diode 40 positioned to direct microwave radiation into a microwave cavity 41, and with a vacuum source shown as the pump 42 connected to the reaction vessel 22 in the cavity 41. Although the microwave source is illustrated as a diode (an IMPATT diode is exemplary), a magnetron is a similarly acceptable source as is a klystron, each of these items being well understood in the art by the skilled person and can be selected as desired for purposes of convenience, design, or cost, and without undue experimentation.

FIG. 6 also shows that microwave radiation from the source 40 is typically directed through a waveguide 43 which provides support to the cavity 41. The vacuum pump 42 pulls from the vessel 22 along line 44 and usually includes a trap 45 which is otherwise conventional (e.g., a cold trap using liquid nitrogen) and positioned between the vessel and the vacuum pump 42. In the absence of the trap 45, the vacuum pump needs to be capable of handling the evaporated base and solvents while still operating as intended.

As schematically illustrated in FIG. 6, in exemplary embodiments, the cavity 41 can support a single mode of microwave radiation at the microwave frequencies produced by the microwave source 40. A temperature probe 46 (for which a fiber optic device is exemplary) is positioned to read the temperature of the reaction vessel 22 in the cavity 41. In conjunction with a processor 47 (which can be either internal or external to the overall system), the measured temperature can be used to drive the source and to thus increase, decrease, or otherwise moderate the microwave radiation into the cavity in the most advantageous manner.

As further schematic details, the microwave source 40 is driven by a power supply broadly designated at 50 which in preferred embodiments can be the switching power supply (and associated methods) set forth in U.S. Pat. No. 6,288,379, the contents of which are incorporated entirely herein by reference. The basic circuits between the power supply and the diode 40 are likewise illustrated schematically at 51. Basic circuitry of the type required is well understood by those in the relevant arts, need not be described in detail herein, and can be built and operated by the skilled person without undue experimentation.

FIG. 7 schematically illustrates a few additional details of the system for carrying out the method of the invention. In FIG. 7 the vessel is again designated at 22, and FIG. 7 further illustrates that the vessel 22 includes a frit 52 (typically made of glass) and a spray head 53. The frit 52 permits liquids to be drained from the reaction vessel 22 and the spray head 53 delivers compositions to the reaction vessel 22. Other equivalent fixtures can be selected by the skilled person without undue experimentation.

In particular, FIG. 7 illustrates a nitrogen supply 54 which is connected to a plurality of supply bottles 55 which for schematic purposes are illustrated as Erlenmeyer flasks. A plurality of metered loops are schematically illustrated by lines 56, 57, and 58 and connect the nitrogen supply to the supply bottles 55; and corresponding lines 60, 61, and 62 then connect to a common line 63 that reaches the spray head 53 for delivery to the vessel 22. A separate line 63 provides nitrogen from the source 54 to the liquids and resin in the vessel 22 to agitate (bubble) the contents of the vessel 22 to carry out appropriate mixing and circulation during deprotection, coupling, and cleavage reactions.

Nitrogen is helpful under these circumstances because it is relatively inexpensive, widely available, and inert to the reactions being carried out and to the equipment in the instrument or system. It will thus be understood that other inert gases, including the noble gases, can be used for this purpose, but in most cases will simply be more expensive and less widely available. In a functional sense, any gas that will avoid interfering chemically with the ongoing reactions or with the instrument will be appropriate.

In a manner consistent with the diagram of FIG. 6, the nitrogen supply and the metered loop can connect to the processor 47 so that the processor 47 can control the manner in which the compositions are dispensed from the vessels 55 to the reaction vessel 52. Although not illustrated, the skilled person will recognize that the simple schematic line connections (64 and 65) are in practice combination of tubes (pipes), valves, and controls for those lines; e.g., in practice line 64 represents a connection between a valve or manifold in line 58, a controller for that line, and the processor 47. The same relationships hold true for the line 65 between the nitrogen supply 54 and the processor 47.

Experimental (Predictive)

Materials and Methods

Reagents

All Fmoc amino acids were obtained from Novabiochem (San Diego, Calif.) and contained the following side chain protecting groups: Asn(Trt), Asp(OtBu), Arg(Pbf), Cys(Trt), Gln(Trt), Glu(OtBu), His(Trt), Lys(Boc), Ser(tBu), Thr (tBu), Trp(Boc), and Tyr(tBu). N-[(1H-Benzotriazol-1-yl) (dimethylamino)methylene]-N-methylmethanaminium hexafluorophosphate Noxide (HBTU), N-hydroxybenzotriazole (HOBt), and benzotriazol-1-yl-N-oxy-tris(pyrrolidino)phosphonium hexafluorophosphate (PyBOP), were also obtained from Novabiochem. Diisopropylethylamine (DIEA), N-methylmorpholine (NMM), collidine (TMP), piperidine, piperazine, trifluoroacetic acid (TFA), thioanisole, 1,2-ethanedithiol (EDT), and phenol were obtained from Sigma Aldrich (St. Louis, Mo.). Dichloromethane (DCM), N,N-Dimethylformamide (DMF), Nmethylpyrrolidone (NMP), anhydrous ethyl ether, acetic acid, HPLC grade water, and HPLC grade acetonitrile were obtained from VWR (West Chester, Pa.).

SPHERITIDE™ resin: Trityl linker was prepared using SPHERITIDE™ resin (CEM Corporation; Matthews, N.C.; USA). The SPHERITIDE™ resin consists of poly-e-lysine cross-linked with multifunctional carboxylic acids.

CEM LIBERTY™ Automated Microwave Peptide Synthesizer

The LIBERTY™ system (CEM Corporation, Matthews, N.C.) is a sequential peptide synthesizer capable of complete automated synthesis including cleavage of up to 12 different peptides. The LIBERTY™ system uses the single-mode microwave reactor, DISCOVER™, which has been widely used in the organic synthesis industry. The LIBERTY™ synthesizer uses a standard 30 milliliter (ml) Teflon® glass fritted reaction vessel for 0.025-1.0 millimole (mmol) syntheses. The reaction vessel features a spray head for delivery of all reagents and a fiber-optic temperature probe for controlling the microwave power delivery. The system utilizes up to 25 stock solutions for amino acids and seven reagent ports that can perform the following functions: main wash, secondary wash, deprotection, capping, activator, activator base, and cleavage. The system uses nitrogen pressure for transfer of all reagents and to provide an inert environment during synthesis. Nitrogen bubbling is used for mixing during deprotection, coupling, and cleavage reactions. The system uses metered sample loops for precise delivery of all amino acid, activator, activator base, and cleavage solutions. The LIBERTY™ synthesizer is controlled by an external computer, which allows for complete control of each step in every cycle.

Peptide Synthesis: (SEQ ID NO: 1) VYWTSPFMKLIHEQCNRADG.NH2

A model peptide containing all 20 amino acids was synthesized under a variety of conditions using the CEM LIBERTY™ automated microwave peptide synthesizer on 0.152 g Spheritide™ resin (0.66 meq/g substitution). Deprotection was performed in two stages using a fresh reagent each time with (i) 80% piperidine in DMF; or (ii) piperidine neat. In each case, 0.8 ml of the piperidine was added to 4.0 ml of the coupling solution remaining from the addition of the previous acid. An initial deprotection of 30 s at 50 W (5 min at 0 W for conventional synthesis) was followed by a 3-min deprotection at 50 W (15 min at 0 W for conventional synthesis) with a maximum temperature of 80° C.

No draining step was carried out between the coupling step of a previous cycle and the addition of the piperidine for the successive cycle.

After deprotection, the piperidine was removed by applying a vacuum that reduced the ambient pressure in the reaction vessel to below atmospheric pressure. Removal was enhanced by applying microwave power at 50 W for 3 minutes.

Coupling reactions were performed in the presence of a 5-fold molar excess of 0.2 M Fmoc-protected amino acids dissolved in DMF with various types of activation: (i) HBTU:DIEA:AA (0.9:2:1); HBTU:HOBt:DIEA:AA (0.9:1:2:1); (iii) PyBOP:DIEA:AA (0.9:2:1); (iv) HBTU:NMM:AA (0.9:2:1); and (v) HBTU:TMP:AA (0.9:21), double coupling on valine. Coupling reactions were for 5 min at 40 W (30 min at 0 W for conventional synthesis) with a maximum temperature of 80° C. In later experiments, coupling conditions of cysteine and histidine were altered to 2 min at 0 W followed by 4 min at 40 W with a maximum temperature of 50° C. Cleavage was performed using 10 ml of Reagent K (TFA/phenol/water/thioanisole/EDT; 82.5/5/5/5/2.5) for 180 min. Following cleavage, peptides were precipitated out and washed using ice-cold anhydrous ethyl ether.

Peptide Analysis

Prior to LC-MS analysis, all peptides were dissolved in 10% acetic acid solution and lyophilized to dryness. Analytical HPLC of peptide products was performed using a Waters Atlantis dC18 column (3 μm, 2.1×100 mm) at 214 nm. Separation was achieved by gradient elution of 5-60% solvent B (solvent A=0.05% TFA in water; solvent B=0.025% TFA in acetonitrile) over 60 min at a flow rate of 0.5 ml/min. Mass analysis was performed using an LCQ Advantage ion trap mass spectrometer with electrospray ionization (Thermo Electron, San Jose, Calif.). Racemization analysis of amino acids was performed by C.A.T. GmbH & Co. (Tuebingen, Germany) using a published GC-MS method that involves hydrolysis of the peptide in 6 N DCl/D2O (*The Peptides: Analysis, Synthesis, Biology*, ERHARD GROSS editor).

In another embodiment, the invention presents a novel process whereby the coupling and deprotection steps occur within the same solvent. In this process concentrated base is added directly to the resin coupling solution after a desired period of time for the coupling to occur. The deprotection step is then immediately started when the base is added. Therefore, the onset of the deprotection step is immediately after the coupling step without any time delay. Additionally, only a small volume of base is required since it can use the solvent present from the coupling reaction. This requires a sophisticated reagent delivery system for the base that is accurate at very small volumes (0.5 mL) with rapid delivery. Typically, a 20% solution of base (piperidine) in solvent is used for the deprotection step. Excess base concentration can increase base-catalyzed side reactions and therefore significant solvent is required. This means that significant solvent can be saved from this process by adding concentrated base to the coupling solvent.

To demonstrate the effectiveness of this new process a batch of 24 peptides were assembled using an automated peptide synthesizer modified to perform the in-situ solvent recycling step during each cycle.

Materials and Methods

All peptides were synthesized using a Liberty Blue PRIME system (CEM Corporation; Matthews, N.C.; USA) allowing for automated in-situ solvent recycling and evaporation based washing. The peptides were synthesized at 0.05 mmol scale with 10 equivalents of amino acid using CarboMAX™ coupling with AA/DIC/Oxyma (1:2:1) based activation for 100 sec at 90° C. ProTide resins (CEM Corporation; Matthews, N.C.; USA) based on TentaGel® technology were used for synthesis with either a Rink Amide linker or a Cl-TCP(Cl) linker with unactivated loading of the first amino acid with DIEA at 90° C. for 5 min. The deprotection step was performed for 50 sec at 95° C. and initiated by adding 0.5 mL of 50% pyrrolidine directly to the coupling solution. A single 1×4 mL wash was used in between the deprotection and coupling steps. Peptides were cleaved with TFA/TIS/H2O/DODt (92.5:2.5:2.5:2.5) for 30 min at 38° C. using a RAZOR cleavage system (CEM Corporation; Matthews, N.C.; USA).

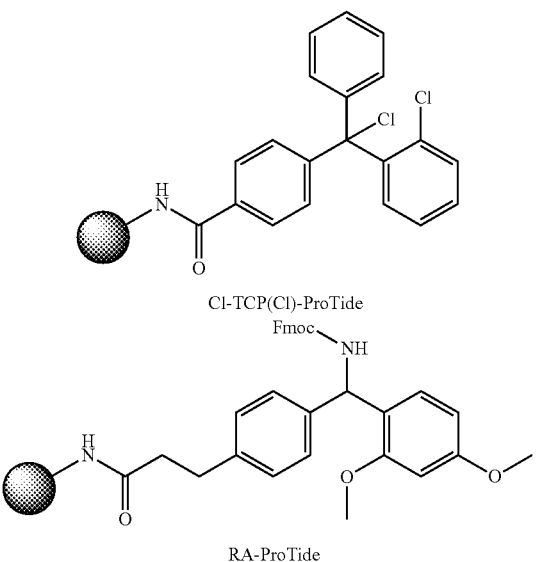

Cl-TCP(Cl)-ProTide

RA-ProTide

Results and Discussion:

All peptides synthesized in Table 1 gave the desired target as the major peak with a standard cycle time of 2 minutes and 58 seconds. The in-situ solvent recycling process allowed for 0.5 mL of a concentrated pyrrolidine (BP 87° C.) solution to be added to the end of the coupling step (without draining) An advantage of this setup was that the deprotection immediately proceeded very close to the desired temperature (95° C.) since the coupling solution was already at 90° C. During the deprotection process a vacuum was applied and the pyrrolidine was evaporated and subsequently condensed in the waste container. This allowed only a single wash step (1×4 mL) to be required at the end of the deprotection step.

TABLE 1

Automated Sequential Batch Synthesis of 24 Peptides

| # | Peptide | Disease Area | Resin Used | UPLC Purity (%) | Synthesis Time |
|---|---------|--------------|------------|-----------------|----------------|
| 1 | GRP (SEQ ID NO: 2) VPLPAGGGTVLTKMYPRGNHWAVGHLM-NH$_2$ | Regulates Gastrin Release | RA ProTide | 81 | 1:22 |
| 2 | Glucagon (SEQ ID NO: 3) H-HSQGTFTSDYSKYLDSRRAQDFVQWLMNT-NH$_2$ | Hypoglycemia | RA ProTide | 75 | 1:28 |

TABLE 1-continued

Automated Sequential Batch Synthesis of 24 Peptides

| # | Peptide | Disease Area | Resin Used | UPLC Purity (%) | Synthesis Time |
|---|---------|--------------|------------|-----------------|----------------|
| 3 | Bivalirudin (SEQ ID NO: 4) H-fPRPGGGNGDFEEIPEEYL-OH | Blood thinner | Cl-2-Cl-Trt | 71 | 1:05 |
| 4 | Angiotensin (SEQ ID NO: 5) H-NRVYVHPF-OH | Vasoconstrictor | Cl-2-Cl-Trt | 82 | 0:30 |
| 5 | PTH 1-34 (SEQ ID NO: 6) H-SVSEIQLMHNLGKHLNSMERVEWLRKKLQDVHNF-$NH_2$ | Osteoporosis | RA ProTide | 70 | 1:43 |
| 6 | Gonadorelin (SEQ ID NO: 7) pEHWSYGLRPG-$NH_2$ | Fertility | RA ProTide | 91 | 0:35 |
| 7 | Triptorelin (SEQ ID NO: 8) pEHWSYwLRPG-$NH_2$ | Breast Cancer, Prostate Cancer, Fertility | RA ProTide | 73 | 0:35 |
| 8 | Liraglutide (SEQ ID NO: 9) H-HAEGTFTSDVSSYLEGQAAK(γ-E-palmitoyl)EFIAWLVRGRG-$NH_2$ | Diabetes | RA ProTide | 80 | 1:31 |
| 9 | Exenatide (SEQ ID NO: 10) H-HGEGTFTSDLSKQMEEEAVRLFIEWLKNGGPSSGAPPPS-$NH_2$ | Diabetes | RA ProTide | 74 | 1:58 |
| 10 | MOG (35-55) (SEQ ID NO: 11) H-MEVGWYRSPFSRVVHLYRNGK-$NH_2$ | Multiple Sclerosis | RA ProTide | 71 | 1:05 |
| 11 | Secretin (SEQ ID NO: 12) H-HDGTFTSELSRLRDSARLQRLLQGLV-$NH_2$ | Osmoregulation | RA ProTide | 70 | 1:19 |
| 12 | Teriparatide (SEQ ID NO: 13) H-SVSEIQLMHNLGKHLNSMERVEWLRKKLQDVHNF-$NH_2$ | Osteoporosis | RA ProTide | 60 | 1:43 |
| 13 | GLP-1 (7-37) (SEQ ID NO: 14) H-HAEGTFTSDVSSYLEGQAAKEFIAWLVKGRG-$NH_2$ | Diabetes | RA ProTide | 74 | 1:34 |
| 14 | Magainin 1 (SEQ ID NO: 15) H-GIGKFLHSAGKFGKAFVGEIMKS-$NH_2$ | Antibiotic | RA ProTide | 79 | 1:11 |
| 15 | Tetracosactide (SEQ ID NO: 16) H-SYSMEHFRWGKPVGKKRRPVKVYP-$NH_2$ | Adrenal Cortex stimulant | RA ProTide | 77 | 1:13 |
| 16 | [Arg8]-Vasopressin (SEQ ID NO: 17) H-CYFQNCPRG-$NH_2$ | Hormone (blood vessel contraction) | RA ProTide | 94 | 0:32 |
| 17 | Ubiquitin (SEQ ID NO: 18) MQIFVKTLTGKTITLEVEPSDTIENVKAKIQDKEGIPPDQQRLIFAGKQLEDGRTLSDYNIQKESTLHLVLRLRGG-$NH_2$ | Protein signaling agent | RA ProTide | ≥60 | 3:44 |
| 18 | Parasin I (SEQ ID NO: 19) H-KGRGKQGGKVRAKAKTRSS-$NH_2$ | Antibiotic | RA ProTide | 87 | 0:59 |
| 19 | Dynorphin A (SEQ ID NO: 20) H-YGGFLRRIRPKLKWDNQ-$NH_2$ | Opioid Research | RA ProTide | 71 | 0:53 |
| 20 | ACP (SEQ ID NO: 21) H-VQAAIDYING-$NH_2$ | Fatty Acid Synthesis | RA ProTide | 92 | 0:32 |
| 21 | BAM 3200 (SEQ ID NO: 22) H-YGGFMRRVGRPEWWMDYQKRYGGFL-$NH_2$ | Opioid Research | RA ProTide | 70 | 1:16 |
| 22 | HIV-TAT (47-57) (SEQ ID NO: 23) Fmoc-YGRKKRRQRRR-$NH_2$ | HIV/AIDS Research | RA ProTide | 93 | 0:31 |

TABLE 1-continued

Automated Sequential Batch Synthesis of 24 Peptides

| # | Peptide | Disease Area | Resin Used | UPLC Purity (%) | Synthesis Time |
|---|---|---|---|---|---|
| 23 | HIV-TAT (48-60) (SEQ ID NO: 24) Fmoc-GRKKRRQRRRPPQ-NH$_2$ | HIV/AIDS Research | RA ProTide | 88 | 0:39 |
| 24 | Pramlintide (SEQ ID NO: 25) KCNTATCATQRLANFLVHSSNNFGPILPPTN VGSNTY--NH$_2$ | Diabetes | RA ProTide | 72 | 1:52 |

TOTAL SYNTHESIS TIME FOR ENTIRE BATCH: 32.6 hours

This new process provided a significant reduction in standard cycle time (2 minutes 57 seconds) from (a)—elimination of the coupling drain time, (b)—elimination of the deprotection delivery time between steps, and (c)—elimination of the temperature ramp time for the deprotection step thereby allowing a shorter deprotection time to be used. Additionally, significant solvent savings were possible with the complete elimination of the deprotection solvent during each cycle.

In the drawings and specification there has been set forth a preferred embodiment of the invention, and although specific terms have been employed, they are used in a generic and descriptive sense only and not for purposes of limitation, the scope of the invention being defined in the claims.

The invention claimed is:

1. A method of deprotection in solid phase peptide synthesis in which the improvement comprises:
adding an organic base deprotection composition neat to a mixture of a growing peptide chain, a solid phase support, and any excess activated amino acid from a preceding coupling cycle;
wherein the organic base is added to the mixture in a volume of 20% or less of the volume of the mixture; and
without any draining step between the coupling step of any preceding coupling cycle and the addition of a deprotection composition for any successive cycle.

2. A method according to claim 1 further comprising adding a successive amino acid to the mixture of the growing peptide chain, the solid phase support, and any excess activated amino acid from a preceding coupling cycle following the step of adding the deprotection composition.

3. A method according to claim 1 comprising adding an organic base selected from the group consisting of piperidine, pyrrolidine, and 4-methyl piperidine.

4. A method according to claim 1 wherein the organic base is a liquid added neat to the mixture of the growing peptide chain, the solid phase support, and any excess activated amino acid from a preceding coupling cycle in a ratio of between about 1:20 and 1:3 based upon the volume of the mixture.

5. A method according to claim 3 comprising adding an organic base selected from the group consisting of piperidine, pyrrolidine, and 4-methyl piperidine in a volume ratio of about 1:5 based upon the volume of the mixture.

6. A method according to claim 1 wherein the volume of the deprotection composition is less than 2 mL.

7. A method according to claim 1 wherein the volume of the deprotection composition is less than 1 mL.

8. A method according to claim 1 wherein the volume of the deprotection composition is between about 0.4 and 1.0 ml added to between about 3.8 and 4.2 ml of the mixture of the growing peptide chain, the solid phase support, and any excess activated amino acid.

9. A method of deprotection in solid phase peptide synthesis in which the improvement comprises:
deprotecting a protected amino acid by combining and heating the protected amino acid and a liquid organic base in a reaction vessel; and
during or after the deprotecting step, reducing the ambient pressure in the vessel with a vacuum pull to remove the liquid organic base without any intervening draining step while simultaneously heating the vessel contents; and
without otherwise adversely affecting the remaining materials in the vessel or causing problems in any subsequent steps in the SPPS cycle.

10. A method according to claim 9 comprising:
applying microwave radiation to heat the deprotection step; and
applying microwave radiation to accelerate the vacuum removal step.

11. A method according to claim 9 comprising reducing the pressure in the vessel to less than one atmosphere.

12. A method according to claim 9 comprising:
heating the combined protected amino acid and liquid organic base to between about 81° C. and 99° C. to accelerate the deprotection step; and
heating the vessel contents to between about 90° C. and 110° C. to accelerate the removal step.

13. A method of deprotection in solid phase peptide synthesis (SPPS) in which the improvement comprises deprotecting in a reaction vessel a protected amino acid below atmospheric pressure at a temperature of at least about 60° C. while providing a path for evaporating base to leave the reaction vessel.

14. A method according to claim 13 further comprising carrying out a maximum of one washing step between the deprotecting and coupling steps in the SPPS cycle.

* * * * *

SEQUENCE LISTING

```
<160> NUMBER OF SEQ ID NOS: 25

<210> SEQ ID NO 1
<211> LENGTH: 20
<212> TYPE: PRT
<213> ORGANISM: Artificial Sequence
<220> FEATURE:
<223> OTHER INFORMATION: Synthetic

<400> SEQUENCE: 1

Val Tyr Trp Thr Ser Pro Phe Met Lys Leu Ile His Glu Gln Cys Asn
1               5                   10                  15

Arg Ala Asp Gly
            20

<210> SEQ ID NO 2
<211> LENGTH: 27
<212> TYPE: PRT
<213> ORGANISM: Artificial Sequence
<220> FEATURE:
<223> OTHER INFORMATION: Synthesized

<400> SEQUENCE: 2

Val Pro Leu Pro Ala Gly Gly Gly Thr Val Leu Thr Lys Met Tyr Pro
1               5                   10                  15

Arg Gly Asn His Trp Ala Val Gly His Leu Met
            20                  25

<210> SEQ ID NO 3
<211> LENGTH: 29
<212> TYPE: PRT
<213> ORGANISM: Artificial Sequence
<220> FEATURE:
<223> OTHER INFORMATION: Synthesized

<400> SEQUENCE: 3

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25
```

<210> SEQ ID NO 4
<211> LENGTH: 20
<212> TYPE: PRT
<213> ORGANISM: Artificial Sequence
<220> FEATURE:
<223> OTHER INFORMATION: Synthesized

<400> SEQUENCE: 4

Phe Pro Arg Pro Gly Gly Gly Gly Asn Gly Asp Phe Glu Glu Ile Pro
1               5                   10                  15

Glu Glu Tyr Leu
            20

<210> SEQ ID NO 5
<211> LENGTH: 8
<212> TYPE: PRT
<213> ORGANISM: Artificial Sequence
<220> FEATURE:
<223> OTHER INFORMATION: Synthesized

<400> SEQUENCE: 5

Asn Arg Val Tyr Val His Pro Phe
1               5

<210> SEQ ID NO 6
<211> LENGTH: 34
<212> TYPE: PRT
<213> ORGANISM: Artificial Sequence
<220> FEATURE:
<223> OTHER INFORMATION: Synthesized

<400> SEQUENCE: 6

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His Asn Phe
            20                  25                  30

<210> SEQ ID NO 7
<211> LENGTH: 10
<212> TYPE: PRT
<213> ORGANISM: Artificial Sequence
<220> FEATURE:
<223> OTHER INFORMATION: Synthesized

<400> SEQUENCE: 7

Glu His Trp Ser Tyr Gly Leu Arg Pro Gly
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthesized

<400> SEQUENCE: 8

Glu His Trp Ser Tyr Trp Leu Arg Pro Gly
1               5                   10

<210> SEQ ID NO 9
<211> LENGTH: 31
<212> TYPE: PRT
<213> ORGANISM: Artificial Sequence
<220> FEATURE:
<223> OTHER INFORMATION: Synthesized -continued

```
<400> SEQUENCE: 9

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 10
<211> LENGTH: 39
<212> TYPE: PRT
<213> ORGANISM: Artificial Sequence
<220> FEATURE:
<223> OTHER INFORMATION: Synthesized

<400> SEQUENCE: 10

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 11
<211> LENGTH: 21
<212> TYPE: PRT
<213> ORGANISM: Artificial Sequence
<220> FEATURE:
<223> OTHER INFORMATION: Synthesized

<400> SEQUENCE: 11

Met Glu Val Gly Trp Tyr Arg Ser Pro Phe Ser Arg Val Val His Leu
1               5                   10                  15

Tyr Arg Asn Gly Lys
            20

<210> SEQ ID NO 12
<211> LENGTH: 26
<212> TYPE: PRT
<213> ORGANISM: Artificial Sequence
<220> FEATURE:
<223> OTHER INFORMATION: Synthesized

<400> SEQUENCE: 12

His Asp Gly Thr Phe Thr Ser Glu Leu Ser Arg Leu Arg Asp Ser Ala
1               5                   10                  15

Arg Leu Gln Arg Leu Leu Gln Gly Leu Val
            20                  25

<210> SEQ ID NO 13
<211> LENGTH: 34
<212> TYPE: PRT
<213> ORGANISM: Artificial Sequence
<220> FEATURE:
<223> OTHER INFORMATION: Synthesized

<400> SEQUENCE: 13

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 14
```

<211> LENGTH: 31
<212> TYPE: PRT
<213> ORGANISM: Artificial Sequence
<220> FEATURE:
<223> OTHER INFORMATION: Synthesized

<400> SEQUENCE: 14

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 15
<211> LENGTH: 23
<212> TYPE: PRT
<213> ORGANISM: Artificial Sequence
<220> FEATURE:
<223> OTHER INFORMATION: Synthesized

<400> SEQUENCE: 15

Gly Ile Gly Lys Phe Leu His Ser Ala Gly Lys Phe Gly Lys Ala Phe
1               5                   10                  15

Val Gly Glu Ile Met Lys Ser
            20

<210> SEQ ID NO 16
<211> LENGTH: 24
<212> TYPE: PRT
<213> ORGANISM: Artificial Sequence
<220> FEATURE:
<223> OTHER INFORMATION: Synthesized

<400> SEQUENCE: 16

Ser Tyr Ser Met Glu His Phe Arg Trp Gly Lys Pro Val Gly Lys Lys
1               5                   10                  15

Arg Arg Pro Val Lys Val Tyr Pro
            20

<210> SEQ ID NO 17
<211> LENGTH: 9
<212> TYPE: PRT
<213> ORGANISM: Artificial Sequence
<220> FEATURE:
<223> OTHER INFORMATION: Synthesized

<400> SEQUENCE: 17

Cys Tyr Phe Gln Asn Cys Pro Arg Gly
1               5

<210> SEQ ID NO 18
<211> LENGTH: 76
<212> TYPE: PRT
<213> ORGANISM: Artificial Sequence
<220> FEATURE:
<223> OTHER INFORMATION: Synthesized

<400> SEQUENCE: 18

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
            50                  55                  60

Ser Thr Leu His Leu Val Leu Arg Leu Arg Gly Gly
 65                  70                  75

<210> SEQ ID NO 19
<211> LENGTH: 19
<212> TYPE: PRT
<213> ORGANISM: Artificial Sequence
<220> FEATURE:
<223> OTHER INFORMATION: Synthesized

<400> SEQUENCE: 19

Lys Gly Arg Gly Lys Gln Gly Gly Lys Val Arg Ala Lys Ala Lys Thr
 1               5                  10                  15

Arg Ser Ser

<210> SEQ ID NO 20
<211> LENGTH: 17
<212> TYPE: PRT
<213> ORGANISM: Artificial Sequence
<220> FEATURE:
<223> OTHER INFORMATION: Synthesized

<400> SEQUENCE: 20

Tyr Gly Gly Phe Leu Arg Arg Ile Arg Pro Lys Leu Lys Trp Asp Asn
 1               5                  10                  15

Gln

<210> SEQ ID NO 21
<211> LENGTH: 10
<212> TYPE: PRT
<213> ORGANISM: Artificial Sequence
<220> FEATURE:
<223> OTHER INFORMATION: Synthesized

<400> SEQUENCE: 21

Val Gln Ala Ala Ile Asp Tyr Ile Asn Gly
 1               5                  10

<210> SEQ ID NO 22
<211> LENGTH: 25
<212> TYPE: PRT
<213> ORGANISM: Artificial Sequence
<220> FEATURE:
<223> OTHER INFORMATION: Synthesized

<400> SEQUENCE: 22

Tyr Gly Gly Phe Met Arg Arg Val Gly Arg Pro Glu Trp Trp Met Asp
 1               5                  10                  15

Tyr Gln Lys Arg Tyr Gly Gly Phe Leu
                 20                  25

<210> SEQ ID NO 23
<211> LENGTH: 11
<212> TYPE: PRT
<213> ORGANISM: Artificial Sequence
<220> FEATURE:
<223> OTHER INFORMATION: Synthesized

<400> SEQUENCE: 23

Tyr Gly Arg Lys Lys Arg Arg Gln Arg Arg
 1               5                  10

```
<210> SEQ ID NO 24
<211> LENGTH: 13
<212> TYPE: PRT
<213> ORGANISM: Artificial Sequence
<220> FEATURE:
<223> OTHER INFORMATION: Synthesized

<400> SEQUENCE: 24

Gly Arg Lys Lys Arg Arg Gln Arg Arg Arg Pro Pro Gln
1               5                   10

<210> SEQ ID NO 25
<211> LENGTH: 37
<212> TYPE: PRT
<213> ORGANISM: Artificial Sequence
<220> FEATURE:
<223> OTHER INFORMATION: Synthesized

<400> SEQUENCE: 25

Lys Cys Asn Thr Ala Thr Cys Ala Thr Gln Arg Leu Ala Asn Phe Leu
1               5                   10                  15

Val His Ser Ser Asn Asn Phe Gly Pro Ile Leu Pro Pro Thr Asn Val
            20                  25                  30

Gly Ser Asn Thr Tyr
            35
```